United States Patent
Kraatz et al.

[11] Patent Number: 5,929,118
[45] Date of Patent: Jul. 27, 1999

[54] FLUOROBUTENIC ACID HYDRAZIDES

[75] Inventors: Udo Kraatz, Leverkusen; Wolfgang Krämer, Burscheid; Wolfram Andersch, Bergisch Gladbach; Andreas Turberg, Erkrath; Norbert Mencke, Leverkusen, all of Germany

[73] Assignee: Bayer Aktiengesellschaft, Leverkusen, Germany

[21] Appl. No.: 09/011,326

[22] PCT Filed: Aug. 5, 1996

[86] PCT No.: PCT/EP96/03456

§ 371 Date: Feb. 9, 1998

§ 102(e) Date: Feb. 9, 1998

[87] PCT Pub. No.: WO97/07091

PCT Pub. Date: Feb. 27, 1997

[30] Foreign Application Priority Data

Aug. 16, 1995 [DE] Germany .................... 195 30 079

[51] Int. Cl.⁶ .................... A61K 31/18; C07C 327/48
[52] U.S. Cl. ................ 514/599; 564/78; 564/84; 564/155; 564/204; 514/602; 514/616
[58] Field of Search ................ 564/155, 78, 84, 564/204; 514/616, 599, 602

[56] References Cited

U.S. PATENT DOCUMENTS 4,950,666  8/1990  Peake et al. .................... 514/227.5
5,389,680  2/1995  Ruminski .................... 514/563
5,514,717  5/1996  Phillion et al. .................... 514/601

FOREIGN PATENT DOCUMENTS

WO 92 15555  9/1992  WIPO .
WO 96 13509  5/1996  WIPO .

*Primary Examiner*—Alan L. Rotman
*Assistant Examiner*—Charanjit S. Aulakh
*Attorney, Agent, or Firm*—Sprung Kramer Schaefer & Briscoe

[57] ABSTRACT

The present invention relates to novel fluorobutenic acid hydrazides of the formula (I)

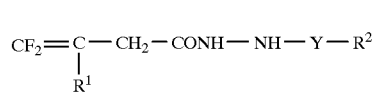

in which

Y represents C=O, C=S or $SO_2$, $R^1$ represents hydrogen or halogen and $R^2$ represents alkyl, halogenoalkyl, alkoxyalkyl, alkylthioalkyl, cycloalkyl, alkenyl, alkenyloxy, alkoxy, cycloalkyloxy, alkylthio or respectively optionally substituted aryl, aralkyl, aralkyloxy or hetaryl, to processes for their preparation and to their use for controlling animal pests.

6 Claims, No Drawings

FLUOROBUTENIC ACID HYDRAZIDES

This application is 371 of PCT/EP96/03456, filed Aug. 5, 1996, which is now published as WO97/07091 on Feb. 27, 1997.

The present invention relates to novel fluorobutenic acid hydrazides, to processes for their preparation and to their use for controlling animal pests, in particular insects, arachnids and nematodes, encountered in agriculture, in forests, in the protection of stored products and materials, and in the hygiene sector.

It is already known that certain fluoroalkenyl compounds have insecticidal, acaricidal and nematicidal activity (cf. for example WO 92/15 555, U.S. Pat. No. 4,952,580, U.S. Pat. No. 4,950,666, U.S. Pat. No. 3,914,251). However, the activity and the activity spectrum of these compounds, in particular at low application rates and concentrations, is not always entirely satisfactory.

This invention, accordingly, provides novel fluorobutenic acid hydrazides of the formula (I)

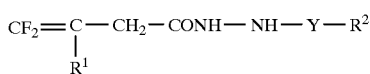
(I)

in which

Y represents C=O, C=S or SO$_2$,

R$^1$ represents hydrogen or halogen and

R$^2$ represents alkyl, halogenoalkyl, alkoxyalkyl, alkylthioalkyl, cycloalkyl, alkenyl, alkenyloxy, alkoxy, cycloalkyloxy, alkylthio or respectively optionally substituted aryl, aralkyl, aralkyloxy or hetaryl.

Depending on the nature of the substituents, the compounds of the formula (I) may be present as geometrical and/or optical isomers or as mixtures of isomers in varying composition. The present invention provides both the pure isomers and the isomer mixtures.

Furthermore, it has been found that the fluorobutenic acid hydrazides of the formula (I) are obtained when A) hydrazides of the formula (II)

R$^2$—Y—NH—NH$_2$ (II)

in which

R$^2$ and Y are each as defined above are reacted with acyl chlorides of the formula (III)

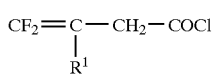
(III)

in which

R$^1$ is as defined above, if appropriate in the presence of a diluent and if appropriate in the presence of a base, or B) acylhydrazines of the formula (IV)

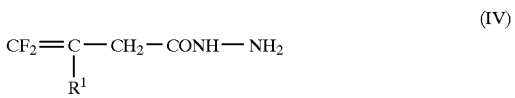
(IV)

in which

R$^1$ is as defined above are reacted with acyl chlorides of the formula (V)

R$^2$—Y—Cl (V)

in which

R$^2$ and Y are each as defined above, if appropriate in the presence of a diluent and if appropriate in the presence of a base.

Finally, it has been found that the novel fluorobutenic acid hydrazides of the formula (I) have very pronounced biological properties and are particularly suitable for controlling animal pests, in particular insects, arachnids and nematodes, encountered in agriculture, in forests, in the protection of stored products and materials, and in the hygiene sector.

The formula (I) provides a general definition of the fluorobutenic acid hydrazides according to the invention.

Preferred substituents or ranges of the radicals listed in the formulae mentioned above and below are illustrated below:

Y preferably represents C=O, C=S or SO$_2$.

R$^1$ preferably represents hydrogen, fluorine, chlorine or bromine.

R$^2$ preferably represents C$_1$–C$_8$-alkyl, C$_1$–C$_8$-halogenoalkyl, C$_1$–C$_6$-alkoxy-C$_1$–C$_6$-alkyl, C$_1$–C$_6$-alkylthio-C$_1$–C$_6$-alkyl, C$_3$–C$_{10}$-cycloalkyl, C$_2$–C$_8$-alkenyl, C$_2$–C$_8$-alkenyloxy, C$_1$–C$_{20}$-alkoxy, C$_3$–C$_{10}$-cycloalkyloxy, C$_1$–C$_{20}$-alkylthio, respectively optionally halogen-, nitro-, cyano-, amino-, hydroxyl-, C$_1$–C$_6$-alkyl-, C$_1$–C$_6$-alkoxy- or C$_1$–C$_6$-alkylthio-substituted phenyl, phenyl-C$_1$–C$_4$-alkyl or phenyl-C$_1$–C$_4$-alkyloxy or optionally halogen- or C$_1$–C$_6$-alkyl-substituted 5- or 6-membered hetaryl, having one or two hetero atoms from the group oxygen, sulphur and nitrogen.

Y particularly preferably represents C=O, C=S or SO$_2$.

R$^1$ particularly preferably represents hydrogen or fluorine.

R$^2$ particularly preferably represents C$_1$–C$_6$-alkyl, C$_3$–C$_6$-cycloalkyl, C$_3$–C$_8$-alkenyl, C$_3$–C$_8$-alkenyloxy, C$_1$–C$_6$-alkoxy, C$_3$–C$_6$-cycloalkyloxy, C$_1$–C$_6$-alkylthio, respectively optionally fluorine-, chlorine-, bromine-, hydroxyl-, C$_1$–C$_4$-alkyl- or C$_1$–C$_4$-alkoxy-substituted phenyl, phenyl-C$_1$–C$_2$-alkyl or phenyl-C$_1$–C$_2$-alkyloxy or respectively optionally C$_1$–C$_4$-alkyl-substituted furanyl, thienyl or pyridyl.

The abovementioned general or preferred radical definitions or illustrations apply to the end products and, correspondingly, to the starting materials and intermediates. These radical definitions can be combined with each other as desired, i.e. including combinations between the respective preferred ranges.

Preference according to the invention is given to the compounds of the formula (I) which contain a combination of the definitions given above as being preferred (preferable).

Particular preference according to the invention is given to the compounds of the formula (I) which contain a combination of the definitions given above as being particularly preferred.

In the radical definitions given above and below, hydrocarbon radicals such as alkyl or alkenyl are in each case—i.e. including in combination with hetero atoms such as alkoxy or alkylthio—straight-chain or branched as far as this is possible.

Using, for example, 3,4,4-trifluorobut-3-enoyl chloride and ethyl carbazate as starting materials for preparing compounds of the formula (I) according to process A), the course of the reaction can be represented by the following scheme:

Using, for example, 3,4,4-trifluorobut-3-enoyl hydrazine and methanesulphonyl chloride as starting materials for preparing compounds of the formula (I) according to process B), the course of the reaction can be represented by the following scheme:

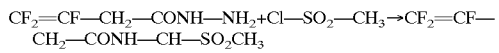

The process A) for preparing compounds of the formula (I) described above is characterized in that hydrazides of the formula (II) are reacted with acyl chlorides of the formula (III), if appropriate in the presence of a diluent and if appropriate in the presence of a base.

The process A) according to the invention is preferably carried out in the presence of a diluent.

Suitable diluents are in particular organic solvents, for example optionally chlorinated aliphatic or aromatic hydrocarbons such as cyclohexane, toluene, xylene, dichloromethane, dichloroethane, chloroform or chlorobenzene, ethers such as diethyl ether, dioxane or tetrahydrofuran, nitriles such as acetonitrile, sulphoxides such as dimethyl sulphoxide or amides such as dimethylformamide.

Suitable diluents are also two-phase systems comprising water and an organic solvent for example water/methylene chloride or water/toluene.

Suitable for use as base are in principle all organic or inorganic bases suitable for such acylation reactions.

Preference is given to amines, in particular tertiary amines such as triethylamine, diazabicycloundecene (DBU), diazabicyclononene (DBN), diazabicyclooctane (DABCO) or pyridine or alkali metal or alkaline earth metal carbonates, bicarbonates or hydroxides. Examples include sodium carbonate, potassium carbonate, sodium bicarbonate, sodium hydroxide, potassium hydroxide and calcium hydroxide.

The reaction temperature in the process A) can be varied over a relatively wide range. In general, the reaction is carried out at temperatures between −10° C. and 160° C., preferably between 0° C. and 100° C.

The molar ratio of the compound of the formula (II) to the compound of the formula (III) is generally 3:1 to 1:3, preferably 1.5:1 to 1:1.5.

The reaction is generally carried out under atmospheric pressure.

For work-up, the reaction mixture is for example hydrolysed and the product is extracted with an organic solvent such as ethyl acetate, dichloromethane or toluene. After removal of the solvent, the crude product may optionally be purified by crystallization or chromatography.

The process B) for preparing compounds of the formula (I) described above is characterized in that acylhydrazines of the formula (IV) are reacted with acyl chlorides of the formula (V), if appropriate in the presence of a diluent and if appropriate in the presence of a base.

Suitable for use as diluents in this process are all solvents or two-phase systems mentioned above for the process A).

Suitable for use as base in this process are all bases mentioned above for the process A).

The reaction temperatures in the process B) described above can be varied over a relatively wide range. In general, the reaction is carried out at temperatures between −10° C. and 160° C., preferably between 0° C. and 100° C.

The molar ratio of the compound of the formula (IV) to the compound of the formula (V) is generally 3:1 to 1:3, preferably 1.5:1 to 1:1.5.

The reaction is generally carried out under atmospheric pressure.

The reaction mixture can be worked up, for example, as described above for the process A).

The hydrazides of the formula (II) required as starting materials for the preparation process A) are known and/or can be prepared in a simple manner by known methods.

The hydrazides of the formula (II) are obtained, for example, by reacting acyl chlorides of the formula (V) with hydrazine.

The acyl chlorides of the formula (III) required as starting materials for the preparation process A) are known (see, for example, U.S. Pat. No. 5,389,680 and EP-432 861).

The acylhydrazines of the formula (IV) required as starting materials for the preparation process B) can be prepared in a simple manner by reacting acyl chlorides of the formula (III) with hydrazine.

The acyl chlorides of the formula (V) are generally known compounds of organic chemistry.

The active compounds are suitable for controlling animal pests, in particular insects, arachnids and nematodes, encountered in agriculture, in forests, in the protection of stored products and of materials, and in the hygiene sector. They can preferably be used as crop protection agents. They are active against normally sensitive and resistant species and against all or some stages of development. The above-mentioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera. for example, *Blatta orientalis, Periplaneta americana, Leucophaea maderae, Blattella germanica, Acheta domesticus*, Gryllotalpa spp., Locusta migratoria migratorioides, Melanoplus differentialis and *Schistocerca gregaria.*

From the order of the Dermaptera, for example, *Forficula auricularia.*

From the order of the Isoptera, for example, Reticulitermes spp.

From the order of the Anoplura, for example, *Pediculus humanus* corporis, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Euryga-ster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorunm, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae.,* Myzus spp., *Phorodon humuli, Rhopalosiphum padi,* Empoasca spp., *Euscelis bilobatus, Nephotettix cincticeps, Lecanium comi, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Bruchidius obtectus, Acanthoscelides obtectus, Hylotrupes bajulus, Agelastica alni,* Leptinotarsadecemlineata, Phaedon cochleariae, Diabrotica spp., Psylliodeschrysocephala, *Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., Drosophilamelanogaster,Musca spp., Fannia spp., Calliphoraerythrocephala, Lucilia spp., Chrysomyia spp., Cuterebra spp., Gastrophilus spp., Hyppobosca spp., Stomoxys spp., Oestrs spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis,* Ceratophyllus spp. and *Ctenocephalides felis.*

From the order of the Arachnida, for example, *Scorpio maurus* and *Latrodectus mactans.*

From the order of the Acarina, for example, Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus The phytoparasiticnematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp. and Trichodorus spp.

The compounds of the formula (I) according to the invention in particular have outstanding nematicidal activity, for example against *Meloidogyne incognita.*

They have systemic action and can be applied via the leaves.

They have good foliar insecticidal action.

The active compounds can be converted to the customary formulations, such as solutions, emulsions, wettable powders, suspensions, powders, dusting agents, pastes, soluble powders, granules, suspo-emulsion concentrates, natural and synthetic materials impregnated with active compound and very fine capsules in polymeric substances.

These formulations are produced in a known manner, for example by mixing the active compounds with extenders, that is liquid solvents and/or solid carriers, if appropriate with the use of surfactants, that is emulsifiers and/or dispersants and/or foam-formers.

In the case of the use of water as an extender, organic solvents can, for example, also be used as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorilloniteor diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, and natural phospholipids, such as cephalins and lecithins, and synthetic phospholipids,can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fuigicides, growth-regulating substances or herbicides. The insecticides include, for example, phosphates, carbamates, carboxylates, chlorinated hydrocarbons, phenylureas and substances produced by microorganisms, inter alia.

Examples of particularly advantageous mixing components are the following:

Fungicides:

2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine. dipyrithione, ditalimfos, dithianon, dodine, drazoxolon, edifenphos, epoxyconazole, ethirimol, etridiazole, fenarimol, fenbuconazole, fenfurarn, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclofos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactencides:

bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Insecticides/Acaincides/Nematicides:

abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin. BPMC, brofenprox, bromophos A, bufencarb, buprofezin, butocarboxim, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimfos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonofos, formothion, fosthiazate, fubfenprox, furathiocarb, HCH, heptenophos, hexaflumuron, hexythiazox, imidacloprid, iprobenfos, isazofos, isofenphos, isoprocarb, isoxathion, ivermectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemeton M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozine, pyrachlofos, pyridaphenthion, pyresmethrin, pyrethrum, pyridaben, pyrimidifen, pyriproxyfen, quinalphos, RH 5992, salithion, sebufos, silafluofen, sulfotep, sulprofos, tebufenozide, tebufenpyrad, tebupirimifos, teflubenzuron, tefluthrin, temephos, terbam, terbufos, tetrachlorvinphos, thiafenox, thiodicarb, thiofanox, thiomethon, thionazin thuringiensin, tralomethrin, triarathene, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth-regulators is also possible.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene and stored-product pests, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp. and Solenopotes spp.

From the order of the Mallophagida and the sub-orders Amblycerina and Ischnocerina, for example, Trimenopon spp., Menopon spp., Trinoton spp., Bovicola spp., Wemeckiella spp., Lepikentron spp., Damalina spp., Trichodectes spp. and Felicola spp.

From the order of the Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanica* and Supella spp.

From the sub-class of the Acaria (Acarida) and the orders of the Meta- and Mesostigmata, for example, Argas spp., Ornithodorus spp., Otabius spp., Ixodes spp., Amblyomma spp., Boophilus spp., Dermacentor spp., Haemaphysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

For example, they have outstanding activity against *Boophilus microplus* and *Lucilia cuprina*.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, caged birds, aquarium fish, and so-called experimental animals, such as, for example, hamsters, guinea-pigs, rats and mice. By controlling these arthropods, it is intended to reduce mortality and decreased performances (in meat, milk, wool, hides, eggs, honey and the like), so that more economical and simpler animal keeping is possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal administration, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders, emulsions, flowables) which comprise the active compounds in an amount of 1 to 80% by weight, either directly or after dilution by a factor of 100 to 10,000, or they may be used in the form of a chemical bath.

The preparation and the use of the active compounds according to the invention are illustrated by the examples below.

PREPARATION EXAMPLES

Example 1

With cooling (0 to 5° C.) and stirring, 4.8 g (30 mmol) of 3,4,4-trifluorobut-3-enoyl chloride dissolved in 10 ml of dichloromethane are added dropwise to a solution of 3.1 g (30 mmol) of ethyl carbazate in 40 ml of dichloromethane and 3.0 g (30 mmol) of triethylamine. The solution is stirred at room temperature overnight and then extracted with ethyl acetate and the organic phase is washed with dilute hydrochloric acid and then with water and concentrated under reduced pressure.

4.0 g of 1-(ethoxycarbonyl)-2-(3,4,4-trifluorobut-3-enoyl)-hydrazine are obtained in a yield of 59% of theory. m.p.: 110° C.

Similarly and/or according to the general preparation procedures, the following compounds of the formula (I) are obtained:

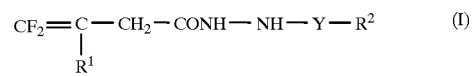

| Ex. No. | R¹ | R² | Y | Physic. Constant |
|---|---|---|---|---|
| 2 | F | CH(CH$_3$)$_2$ | CO | m.p.: 182–184° C. |
| 3 | F | 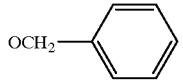 | CO | m.p.: 116° C. |
| 4 | F | OCH$_2$CH$_2$CH$_3$ | CO | m.p.: 84° C. |
| 5 | F | O(CH$_2$)$_2$CH(CH$_3$)$_2$ | CO | m.p.: 74° C. |
| 6 | F | 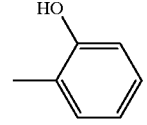 | CO | m.p.: 222° C. |
| 7 | F | 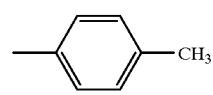 | CO | m.p.: 196° C. |
| 8 | F | 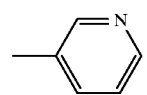 | CO | m.p.: 158° C. |

-continued $$CF_2=C(R^1)-CH_2-CONH-NH-Y-R^2 \quad (I)$$

| Ex. No. | R¹ | R² | Y | Physic. Constant |
|---|---|---|---|---|
| 9 | F | 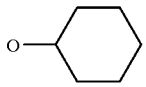 O-cyclohexyl | CO | m.p.: 112° C. |
| 10 | F | OCH₃ | CO | m.p.: 128° C. |
| 11 | F | 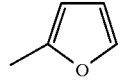 furan-2-yl | CO | m.p.: 122° C. |
| 12 | F | OC(CH₃)₃ | CO | m.p.: 96° C. |
| 13 | F | OCH₂—CH=CH₂ | CO | m.p.: 106° C. |
| 14 | F | 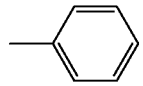 phenyl | CO | m.p.: 110° C. |
| 15 | F | 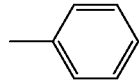 4-Cl-phenyl | CO | m.p.: 188° C. |
| 16 | F |  4-OCH₃-phenyl | CO | m.p.: 180° C. |
| 17 | F | C(CH₃)₃ | CO | m.p.: 114° C. |
| 18 | F | SCH(CH₃)₂ | CO | m.p.: 116° C. |
| 19 | F | 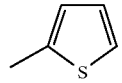 thien-2-yl | CO | m.p.: 186–189° C. |
| 20 | F | SCH₃ | CS | m.p.: 150° C. |
| 21 | F | 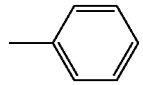 4-CH₃-phenyl | SO₂ | m.p.: 168° C. |
| 22 | F | 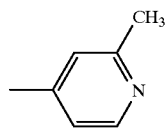 phenyl | SO₂ | m.p.: 190° C. |
| 23 | F | CH₃ | SO₂ | m.p.: 138° C. |
| 24 | F | 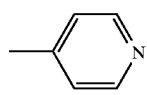 2-CH₃-pyridin-4-yl | CO | m.p.: 154° C. |
| 25 | F | 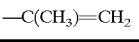 pyridin-4-yl | CO | m.p.: 188° C. |
| 26 | F | —C(CH₃)=CH₂ | CO | m.p.: 134° C. |

USE EXAMPLES

Example A

Critical concentration test/nematodes

Test nematode: Meloidogyne incognita

Solvent: 4 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is heavily infested with the test nematodes. The concentration of the active compound in the preparation is immaterial, only the amount of active compound per unit volume of soil, which is given in ppm (=mg/l), matters. The treated soil is transferred into pots, lettuce is sown in and the pots are kept at a greenhouse temperature of 25° C.

After four weeks, the lettuce roots are checked for infestation with nematodes (root galls) and the efficacy of the active compound in % is determined. The efficacy is 100% when infestation is avoided completely and 0% when the infestation level is just as high as in the control plants in untreated, but equally infested, soil.

In this test an efficacy of 100% was shown, for example, by the compounds of Preparation Examples 3, 7 and 8 at an exemplary active compound concentration of 20 ppm.

Example B

Test with fly larvae/development-inhibitory action

Test animals: All larval stages of Lucilia cuprina (OP resistant) [pupae and adults (without contact with the active compound)]

Solvent: 35 parts by weight of ethylene glycol monomethyl ether

Emulsifier: 35 parts by weight of nonylphenol polyglycol ether

To produce a suitable formulation, three parts by weight of active compound are mixed with seven parts by weight of the abovementioned solvent-emulsifier mixture, and the resulting emulsion concentrate is diluted with water to the desired concentration.

For each individual concentration, 30 to 50 larvae are introduced into a test tube which contains 1 cm³ of horse meat. 500 μl of the dilution to be tested are pipetted onto this horse meat. The test tubes are placed in plastic beakers whose bottom is covered with sea sand, and kept in an air-conditioned room (26° C.±1.5° C., 70% relative humidity ±10%). The activity is examined (larvicidal action) after 24 hours and 48 hours. After emergence of the larvae (about 72 h), the test tubes are removed and perforated plastic lids are fitted onto the beakers. After 1.5 times the development time (hatching of control flies), the hatched flies and the pupae/cocoons are counted.

The activity criterion is the incidence of death in the treated larvae after 48 h (larvicidal effect), or the inhibition of hatching of adults from pupae or the inhibition of pupae formation. The criterion for the in vitro activity of a substance is the inhibition of the development of the flies, or a development standstill before the adult stage. 100% larvicidal action means that all the larvae have been killed after 48 hours. 100% development-inhibitory action means that no adult flies have hatched.

In this test an activity of 100% was shown, for example, by the compounds of Preparation Examples 1, 10 and 14 at an exemplary active compound concentration of 1000 ppm.

Example C

Test with Boophilus microplus-resistant/SP-resistant Parkhurst strain

Test animals: Adult females which have sucked themselves full

Solvent: Dimethyl sulphoxide 20 mg of active compound are dissolved in 1 ml of dimethyl sulphoxide, and lower concentrations are prepared by dilution with the same solvent.

The test is carried out in 5 replications. 1 μl of the solutions is injected into the abdomen, and the animals are transferred into dishes and kept in an air-conditioned room. The activity is determined via the inhibition of oviposition. 100% means that no tick has deposited eggs.

In this test an activity of 100% was shown, for example, by the compounds of Preparation Examples 1, 4, 5, 8, 9, 10, 12, 13, 14 and 15 at an exemplary concentration of 20 μg/animal.

We claim:

1. Compounds of the formula (I)

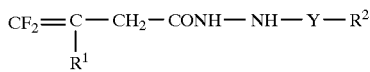
(I)

in which

Y represents C=O, C=S or $SO_2$, $R^1$ represents hydrogen or halogen and $R^2$ represents optionally substituted aryl, aralkyl or aralkyloxy.

2. Compounds of the formula (I) according to claim 1 in which

Y represents C=O, C=S or $SO_2$, $R^1$ represents hydrogen, fluorine, chlorine or bromine and $R^2$ represents optionally halogen-, nitro-, cyano-, amino-, hydroxyl-, $C_1$–$C_6$-alkyl-, $C_1$–$C_6$-alkoxy- or $C_1$–$C_6$-alkylthio-substituted phenyl, phenyl-$C_1$–$C_4$-alkyl or phenyl-$C_1$–$C_4$-alkyloxy.

3. Compounds of the formula (I) according to claim 1 in which

Y represents C=O, C=S or $SO_2$, $R^1$ represents hydrogen or fluorine and $R^2$ represents optionally fluorine-, chlorine-, bromine-, hydroxyl-, $C_1$–$C_4$-alkyl- or $C_1$–$C_4$-alkoxy-substituted phenyl, phenyl-$C_1$–$C_2$-alkyl or phenyl-$C_1$–$C_2$-alkyloxy.

4. Process for preparing compounds of the formula (I) according to claim 1, wherein A) hydrazides of the formula (II)

(II)

in which $R^2$ and Y are each as defined in claim 1 are reacted with acyl chlorides of the formula (III)

(III)

in which $R^1$ is as defined in claim 1, optionally in the presence of a diluent and optionally in the presence of a base, or B) acylhydrazines of the formula (IV)

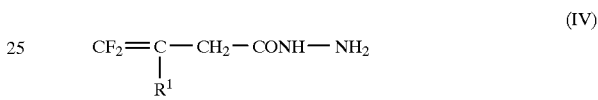
(IV)

in which $R^1$ is as defined in claim 1 are reacted with acyl chlorides of the formula (V)

(V)

in which $R^2$ and Y are each as defined in claim 1, optionally in the presence of a diluent and optionally in the presence of a base.

5. A pesticidal composition comprising a pesticidally effective amount of a compound according to claim 1 and an extender.

6. A method of combating unwanted pests which comprises administering to such pests or to a locus from which it is desired to exclude such pests a pesticidally effective amount of a compound according to claim 1.

* * * * *